United States Patent [19]

Nunn et al.

[11] Patent Number: 4,705,849

[45] Date of Patent: Nov. 10, 1987

[54] BORONIC ACID ADDUCTS OF TECHNETIUM-99M DIOXIME COMPLEXES

[75] Inventors: Adrian D. Nunn, Hopewell; Thomas A. Feld, Califon, both of N.J.; Elizabeth N. Treher, Washington Crossing, Pa.

[73] Assignee: E. R. Squibb & Sons, Inc., Princeton, N.J.

[21] Appl. No.: 723,601

[22] Filed: Apr. 15, 1985

[51] Int. Cl.$^4$ .................. A61K 43/00; A61K 49/02; C07F 13/00

[52] U.S. Cl. ...................................... 534/14; 424/1.1; 422/61

[58] Field of Search .................. 424/1.1, 9; 534/14,10; 422/61

[56] References Cited

U.S. PATENT DOCUMENTS 4,387,087 6/1983 Deutsch et al. ................... 424/1.1
4,419,339 12/1983 Neirinckx ............................ 424/1.1
4,615,876 10/1986 Troutner et al. .................... 424/1.1

OTHER PUBLICATIONS

Deutsch et al, Proc. Natl. Acad. Sci. USA 73(12): 4287–4289, 1976.
Gallop et al, Science 217(9): 166–169, (1982).
Int. J. Appl. Radiat. Isot., vol. 35, No. 6, pp. 467–470, (1984), "A Neutral Lipophilic Complex of $^{99m}$Tc with a Multidentate Amine Oxime".
Isotopenpraxis, 19 (1983) 12, pp. 431–433, "Complexing Properties of Amide Oxime of Picolinic Acid (APA)".
J. Amer. Chem. Soc., 93(18):4411–4415 (1971).
J. Amer. Chem. Soc., 95(13):4163–4168 (1973).
J. Amer. Chem. Soc., 92(11):3500–3502 (1970).
J.C.S. Chem. Comm., p. 1291 (1972), "Simple Direct Syntheses of Iron Clathro–Chelates Derived from Dimethylglyoxime and Boron Compounds", Jackels et al.
Inorg. Chem., vol. 12, No. 6, 1973, p. 1232, "Encapsulation Reactions, Synthesis and Characterization of Clathro Chelates Derived from Iron(II), Dimethylglyoxime & Boron Compounds", Jackels et al.
Inorganic Synthesis, vol. 17, p. 139 (1978), "Other Transition Metal Compounds", Jackels et al.
Inorg. Chem., vol. 24, p. 3381 (1985), "Synthesis and Electrochemistry of Iron(II) Clathrochelates", Robbins et al.
J.A.C.S., vol. 95, p. 4163 (1973), "Encapsulation Reactions, Synthesis and Study of Clathro Chelates Derived from Dimethylglyoxime, Cobalt and Lewis Acids", Boston et al.
Inorg. Synth., vol. 21, p. 112 (1983), "[Tris[u-[(1,2-Cyclohexanedione Dioximato)O:O']Diphenyldiborato(-2-)]-N,N',N'',N''',N'''']Iron(II)", Johnson et al.
Journal of Chem. Soc. (1963), p. 6041, "Hydrogen Bonding in Complexes of Dimethylglyoxime with Cobalt(III)", Gillard et al.

Primary Examiner—John F. Terapane
Assistant Examiner—J. E. Thomas
Attorney, Agent, or Firm—Lawrence S. Levinson; Donald J. Barrack

[57] ABSTRACT

Boronic acid adducts of technetium-99m dioxime complexes are useful for imaging the myocardium, hepatobiliary system, brain and blood pool in humans and other mammalian species.

28 Claims, No Drawings

BORONIC ACID ADDUCTS OF TECHNETIUM-99M DIOXIME COMPLEXES

BRIEF DESCRIPTION OF THE INVENTION

Boronic acid adducts of technetium-99m dioxime complexes having the formula $$^{99m}Tc\ X(Y)_3Z \qquad \text{I}$$

are useful as imaging agents in humans and other mammalian species. In formula I, and throughout the specification, the symbols are as defined below.

X is an anion;
Y is a vicinal dioxime having the formula $$\begin{array}{cc} R_1 & R_2 \\ | & | \\ HO-N=C-C=N-OH, \end{array} \qquad \text{II}$$

or a pharmaceutically acceptable salt thereof, and $R_1$ and $R_2$ are each independently hydrogen, halogen, alkyl, aryl, amino or a 5 or 6-membered nitrogen or oxygen containing heterocycle, or together $R_1$ and $R_2$ are -$(CR_8R_9)_n$- wherein n is 3, 4, 5 or 6 and $R_8$ and $R_9$ are each independently hydrogen or alkyl;

Z is a boron derivative having the formula $$B-R_3 \qquad \text{III}$$

wherein $R_3$ is hydroxy, alkyl, alkenyl, cycloalkyl, cycloalkenyl, alkoxy, carboxyalkyl (preferably having 2 to 19 carbons), carboxyalkenyl (preferably having 4 to 19 carbons), hydroxyalkyl, hydroxyalkenyl, alkoxyalkyl, alkoxyalkenyl, haloalkyl, haloalkenyl, aryl, arylalkyl or and $R_4R_5N$)-alkyl and $R_4$ and $R_5$ are each independently hydrogen, alkyl, or arylalkyl, or $R_4$ and $R_5$ when taken together with the nitrogen atom to which they are attached form a 5 or 6-membered nitrogen containing heterocycle.

Listed below are definitions of the terms used to describe the complexes of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "alkenyl" refers to both straight and branched chain groups. Those groups having 2 to 10 carbon atoms are preferred.

The term "aryl" refers to phenyl and substituted phenyl. Preferred are phenyl and phenyl substituted with 1, 2 or 3 alkyl, haloalkyl, aminoalkyl, alkylaminoalkyl, dialkylaminoalkyl, alkoxy, alkoxyalkyl, halogen, amino, hydroxy, or formyl groups. Additional exemplary aryl groups for the instance wherein $R_3$ is aryl include 3-(5-dimethylamino-1-naphthalenesulfonylamino)phenyl, 3-[4-[3'-phenyl-2'-pyrazolin-1,1'-yl]benzenesulfonyl-amino]phenyl, 3-(pyrenesulfamido)-phenyl, 3-[4-(4-dimethylamino-1-naphthylazo)-3 -(methoxyphenyl-sulfamido)]phenyl, 3-[4-(4-dimethylamino-1-phenylazo)phenylthioureido]phenyl.

Preferred "cycloalkyl" and "cycloalkenyl" groups are those having 5,6 or 7 carbon atoms. The terms include those groups substituted with alkyl, alkoxy, aryl, carboxyalkyl, arylalkyl or ($R_4R_5N$)-alkyl groups.

The terms "halide", "halo" and "halogen" refer to fluorine, chlorine, bromine and iodine.

The expression "5 or 6-membered nitrogen containing heterocycle" refers to all 5 and 6-membered rings containing at least one nitrogen atom. Exemplary aliphatic groups are dehydro derivatives of a compound having the formula

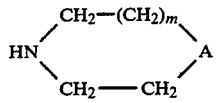

wherein m is 0 or 1 and A is O, N—$R_6$ or CH—$R_6$ wherein $R_6$ is hydrogen, alkyl, aryl or arylalkyl. Such groups include pyrrolidinyl, piperidinyl, morpholinyl, piperazinyl, 4-alkylpiperazinyl, 4-alkylpiperidinyl, and 3-alkylpyrrolidinyl groups. Also included within the expression "5 or 6-membered nitrogen containing heterocycle" are aromatic groups. Exemplary aromatic groups are pyrrolyl, imidazolyl, oxazolyl, pyrazolyl, pyridinyl, and pyrimidinyl groups. The above groups can be linked via a hetero atom or a carbon atom.

The expression "5 or 6-membered nitrogen or oxygen containing heterocycle" refers to all 5 and 6-membered rings containing at least one nitrogen or oxygen atom. Exemplary groups are those described above under the definition of the expression "5 or 6-membered nitrogen containing heterocycle". Additional exemplary groups are 1,4-dioxanyl and furanyl.

DETAILED DESCRIPTION OF THE INVENTION

Preparation of the complexes of this invention can best be accomplished using technetium-99m in the form of the pertechnetate ion. The pertechnetate ion can be obtained from commercially available technetium-99m parent-daughter generators; such technetium is in the +7 oxidation state. The generation of the pertechnetate ion using this type of generator is well known in the art, and is described in more detail in U.S. Pat. Nos. 3,369,121 and 3,920,995. These generators are usually eluted with saline solution and the pertechnetate ion is obtained as the sodium salt.

To prepare the complexes of this invention, pertechnetate ion (in the form of a salt) is combined with a source of anion, a boronic acid derivative having the formula $$\begin{array}{c} R_3 \\ | \\ R_7O-B-OR_7, \end{array} \qquad \text{IV}$$

or a pharmaceutically acceptable salt thereof, wherein $R_7$ is hydrogen, alkyl or aryl, and a dioxime having the formula $$\begin{array}{cc} R_1 & R_2 \\ | & | \\ HO-N=C-C=N-OH, \end{array} \qquad \text{II}$$

or a pharmaceutically acceptable salt thereof.

It is possible, in some instances, to prepare a boronic acid derivative of formula IV in situ. For example, when preparing a complex having an alkoxy group attached to the boron atom, it is possible to utilize boric acid and the appropriate alkanol as reactants.

The source of the anion moiety (X) can be water or it can be an acid or salt which dissociates to release an appropriate anion. Exemplary anionic moieties are hydroxyl, halide, isothiocyanato (N=C=S$^\ominus$) and thiocyanato (S—C=N$^\ominus$). The preferred anionic moieties are the halides, and chloride is the most preferred halide. If the source of the anoin is not water, the source should be present in an appropriate concentration to compete effectively with any water that may be present during the reaction. It has been found that the source of anoin should be present in the reaction mixture in a concentration of about 0.3 to 4.5 molar.

The boronic acid derivative of formula IV should preferably be present in a concentration of about 5 to 200 millimolar. The dioxime of formula II should preferably be present in a concentration. of about 9 to 43 millimolar.

The formation of the complex proceeds best if the mixture of pertechnetate ion, source of anion, boronic acid derivative, and dioxime is heated at about 25° C. to 150° C. for about 5 minutes to about 60 minutes, preferably at about 100° C. to about 140° C. for about 5 minutes to about 15 minutes. The reaction is preferably run in an aqueous medium at a pH of less than, or equal to, about 5.

The reaction mixture should also contain a reducing agent. Stannous ion is the preferred reducing agent, and can be introduced in the form of a stannous salt such as a stannous halide (e.g., stannous chloride or stannous fluoride). The reducing agent should be present in a concentration of about 1.5 micromolar to 6.6 millimolar.

Various complexing agents (also known in the art as chelating agents) can be included as part of the complexing reaction. The complexing agent should, of course, be pharmaceutically acceptable. Exemplary complexing agents are diethylenetriamine-pentaacetic acid (DTPA), ethylene glycol-bis(β-aminoethyl ether)-N,N'-tetraacetic acid (EGTA), ethylenediamine tetraacetic acid (EDTA), citric acid, tartaric acid, malonic acid, etc.

The complexing reaction mixture can also include an accelerator (catalyst) which serves to improve the radiochemical purity (i.e., per cent of the radioactivity that is in the desired chemical form) of the product. Exemplary accelerators are the α-hydroxycarboxylic acids such as citric acid, tartaric acid, and malonic acid. A combination of DTPA and citric acid has been found to be preferred.

Working with the technetium-99 isotope, the structure of complexes of this invention has been investigated and is believed to be:

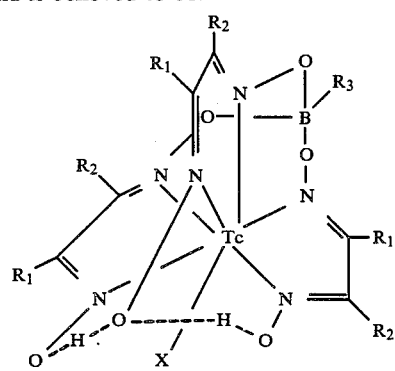

Because of the short half-life of technetium-99m (i.e., 6.02 hours), it is necessary to prepare the complexes of this invention at, or near, the site where they are to be used. A kit having all of the components, other than the pertechnetate ion, needed to prepare the boronic adducts of technetium-99m dioxime complexes of formula I is an integral part of this invention. Such a kit contains a source of anion, a boronic acid derivative of formula IV (or compounds which can react in situ to form such a derivative), or a pharmaceutically acceptable salt thereof, a dioxime of formula II, or a pharmaceutically acceptable salt thereof, and a reducing agent. It may optionally contain a complexing agent.

The kits of this invention can be formulated in aqueous solution. To optimize the stability of the kit, and to optimize the radiochemical purity of the labeled product, the pH of the kit should be adjusted to fall within the range of about 2.0 to 5.5 using a pharmaceutically acceptable acid or base (e.g., hydrochloric acid or sodium hydroxide). Preferably, the pH of the kit will be about 3.0. It is also preferred that the kit be in lyophilized form. While "wet" kits can be used, they are not as efficacious as the corresponding lyophilized kit.

The complexes of this invention are useful as imaging agents. More specifically, they are useful for imaging the myocardium and the hepatobiliary system in humans and other mammalian hosts. Those complexes of this invention which are neutral at physiological pH (i.e., pH 7.4) are also useful for imaging the brain in humans and other mammalian hosts. [The charge of the complexes of this invention is determined by the sum of the charges of the organic groups ("R$_1$", "R$_2$" and "R$_3$") attached to the boron atom and part of the dioximes.] Those complexes of this invention which contain the vicinal dioxime 1,2-ethanedione dioxime are also useful for imaging the blood pool of humans and other mammalian hosts.

The complexes of this invention can be administered to a host by bolus intravenous injection. The size of the host, and the imaging system used, will determine the quantity of radioactivity needed to produce diagnostic images. For a human host, the quantity of radioactivity injected will normally range from about 5 to 20 millicuries of technetium-99m.

The following examples are specific embodiments of this invention.

EXAMPLE 1

99mTc (chlorine)(dimethyl glyoxime)$_3$ methoxy boron and 99mTc (chlorine)(dimethyl glyoxime)$_3$hydroxy boron Into a 5 ml siliconized serum vial were measured 5.0 mg of dimethyl glyoxime, 0.5 ml of methanol, 2.0 mg of boric acid and 0.5 mg of stannous chloride in 5µl of concentrated hydrochloric acid.

Sodium pertechnetate* in physiological saline (0.2 ml) was added to the vial which was then heated at 140° C. for 30 minutes yielding 6%** of the 99mTc (chlorine) (dimethyl glyoxime)$_3$ methoxy boron as determined by HPLC (high pressure liquid chromatography). The reaction also yielded 99mTc (chlorine)(dimethyl glyoxime)$_3$ hydroxy boron. The complexes were separated by HPLC.

*The sodium pertechnetate used in these examples is obtained by eluting a sterile technetium-99m generator with physiological saline.
**As used in these examples, the yield is determined by HPLC and is reported as the precent of radioactivity eluted in the desired form.

EXAMPLE 2

99mTc (chlorine)(dimethyl glyoxime)3 ethoxy boron and 99mTc (chlorine)(dimethyl glyoxime)3hydroxy boron Into a 5 ml siliconized vial were measured 2.0 mg of dimethyl glyoxime in 0.2 ml of ethanol, 2.0 mg of boric acid, 10 mg of citric acid in 0.1 ml of water, 100 mg of sodium chloride, 1.0 mg of diethylenetetramine pentaacetic acid, and approximately 50–60μg of anhydrous stannous chloride in 1μl of concentrated hydrochloric acid.

Sodium pertechnetate in physiological saline (0.5 ml) was added to the vial which was then heated at 100° C. for 5 minutes yielding 4–5% of 99mTc (chlorine)(-dimethyl glyoxime)3 ethoxy boron. The reaction also yielded 99mTc (chlorine)(dimethyl glyoxime)3hydroxy boron. The complexes were separated by HPLC.

EXAMPLE 3

99mTc (chlorine)(dimethyl glyoxime)3 propyloxy boron and 99mTc (chlorine)(dimethyl glyoxime)3-hydroxy boron Following the procedure of example 1, but substituting n-propanol for methanol, yielded 99mTc (chlorine)(dimethyl glyoxime)3 ethoxy boron. The reaction also yielded 99mTc (chlorine)(dimethyl glyoxime)3hydroxy boron. The complexes were separated by HPLC.

EXAMPLE 4

99mTc (chlorine)(dimethyl glyoxime)3 butyloxy boron and 99mTc (chlorine)(dimethyl glyoxime)3hydroxy boron Following the procedure of example 1, but substituting n-butanol for methanol, yielded 6% of 99mTc (chlorine)(dimethyl glyoxime)3 ethoxy boron. The reaction also yielded 99mTc (chlorine)(dimethyl glyoxime)3hydroxy boron. The complexes were separated by HPLC.

EXAMPLE 5

99mTc (chlorine)(dimethyl glyoxime)3 pentyloxy boron and 99mTc (chlorine)(dimethyl glyoxime)3hydroxy boron Following the procedure of example 1, but substituting n-pentanol for methanol, yielded 99mTc (chlorine)(-dimethyl glyoxime)3 ethoxy boron. The reaction also yielded 99mTc (chlorine)(dimethyl glyoxime)3hydroxy boron. The complexes were separated by HPLC.

EXAMPLE 6

99mTc (chlorine)(dimethyl glyoxime)3 hexyloxy boron and 99mTc (chlorine)(dimethyl glyoxime)3hydroxy boron Following the procedure of example 1, but substituting n-hexanol for methanol, yielded 8% of 99mTc (chlorine)(dimethyl glyoxime)3 ethoxy boron. The reaction also yielded 99mTc (chlorine)(dimethyl glyoxime)3hydroxy boron. The complexes were separated by HPLC.

EXAMPLE 7

99mTc (chlorine)(dimethyl glyoxime)3 octyloxy boron and 99mTc (chlorine)(dimethyl glyoxime)3hydroxy boron Following the procedure of example 1, but substituting n-octanol for methanol, yielded 12% 99mTc (chlorine)(dimethyl glyoxime)3 ethoxy boron. The reaction also yielded 99mTc (chlorine)(dimethyl glyoxime)3hydroxy boron. The complexes were separated by HPLC.

EXAMPLE 8

99mTc (chlorine)(dimethyl glyoxime)3 1-methylpropyl boron

Following the procedure of example 2, but substituting 1-methylpropane boronic acid for boric acid, yielded the title complex.

EXAMPLE 9

99mTc (chlorine)(dimethyl glyoxime)3 methyl boron

Into a 5 ml siliconized serum vial were measured 2.0 mg of dimethyl glyoxime in 0.2 ml of ethanol, 2.0 mg of methane boronic acid, 10 mg of citric acid in 0.1 ml of water, 100 mg of sodium chloride, 1.0 mg of diethylenetetramine pentaacetic acid, and about 50–60μg of stannous chloride in 1μl of concentrated hydrochloric acid.

Sodium pertechnetate in physiological saline (0.5 ml) was added to the vial which was heated at 100° C. for 5 minutes yielding 80–90% of the title complex.

EXAMPLE 10

99mTc (chlorine)(dimethyl glyoxime)3 propyl boron

Following the procedure of example 9, but substituting 1-propane boronic acid for methane boronic acid, yielded the title complex.

EXAMPLE 11

99mTc (chlorine)(dimethyl glyoxime)3 butyl boron

Following the procedure of example 9, but substituting 1-butane boronic acid for methane boronic acid, yielded the title complex.

EXAMPLE 12

99mTc (chlorine)(dimethyl glyoxime)3 pentyl boron

Following the procedure of example 9, but substituting 1-pentane boronic acid for methane boronic acid, yielded 85% of the title complex.

EXAMPLE 13

99mTc (chlorine)(dimethyl glyoxime)3 hexyl boron

Into a 5 ml siliconized serum vial were measured 3.0 mg of dimethyl glyoxime, 20 mg of 1-hexane boronic acid, sodium pertechnetate in physiological saline (0.2 ml) and 50μl of saturated aqueous stannous tartrate. The vial was heated at 140° C. for 5 minutes yielding 16% of the title complex.

EXAMPLE 14

99mTc (chlorine)(dimethyl glyoxime)3 heptyl boron

Following the procedure of example 9, but substituting 8.0 mg of 1-heptane boronic acid for methane boronic acid and substituting 50μl of saturated aqueous stannous tartrate for stannous chloride in hydrochloric acid, yielded 85% of the title complex.

EXAMPLE 15

99mTc (chlorine)(dimethyl glyoxime)3 phenyl boron

Following the procedure of example 2, but substituting benzene boronic acid for boric acid, yielded 88% of the title complex.

EXAMPLE 16

99mTc (chlorine)(dimethyl glyoxime)3 butyl boron

Into a 5 ml siliconized serum vial were measured 1.0 mg of dimethyl glyoxime in 0.1 ml of ethanol, 5.0 mg of 1-butane boronic acid in 50$\mu$l of ethanol, 0.3 ml of saturated aqueous sodium chloride and 25$\mu$l of saturated stannous pyrophosphate.

Sodium pertechnetate in physiological saline (0.1 ml) was added to the vial which was heated at 140° C. for 5 minutes yielding 70% of the title complex.

EXAMPLE 17

99mTc (bromine)(dimethyl glyoxime)3 butyl boron

Into a 5 ml siliconized serum vial were measured 1.0 mg of dimethyl glyoxime in 0.1 ml of ethanol, 5.0 mg of 1-butane boronic acid in 50$\mu$l of ethanol, 0.3 ml of saturated aqueous potassium bromide, and 25$\mu$l of saturated aqueous stannous pyrophosphate.

Sodium pertechnetate in physiological saline (0.1 ml) was added to the vial which was heated at 140° C. for 5 minutes yielding 59% of the title complex.

EXAMPLE 18

99mTc (iodine)(dimethyl glyoxime)3 butyl boron

Into a 5 ml siliconized serum vial were measured 1.0 mg of dimethyl glyoxime in 0.1 ml of ethanol, 5.0 mg of 1-butane boronic acid in 50$\mu$l of ethanol, 0.3 ml of saturated aqueous potassium iodide, 25 $\mu$l of saturated aqueous stannous pyrophosphate.

Sodium pertechnetate in physiological saline (0.1 ml) was added to the vial which was heated at 140° C. for 5 minutes yielding 23% of the title complex.

EXAMPLE 19

99mTc (fluorine)(dimethyl glyoxime)3 butyl boron

Into a 5 ml siliconized serum vial were measured 1.0 mg of dimethyl glyoxime in 0.1 ml of ethanol, 5.0 mg 1-butane boronic acid in 50$\mu$l of ethanol, 0.3 ml of saturated aqueous sodium fluoride, and 25$\mu$l of saturated aqeuous stannous pyrophosphate.

Sodium pertechnetate in physiological saline (0.2 ml) was added to the vial which was heated at 140° C. for 5 minutes yielding 0.6% of the title complex.

EXAMPLE 20

99mTc (chlorine)(dimethyl glyoxime)3 3-aminophenyl boron

Into a 5 ml siliconized serum vial were measured 5.0 mg of dimethyl glyoxime in methanol, 30 mg of 3-aminobenzene boronic acid, and 0.5 mg of stannous chloride in 5$\mu$l of concentrated hydrochloric acid.

Sodium pertechnetate in physiological saline (0.2 ml) was added to the vial which was heated at 140° C. for 5 minutes yielding 50% of the title complex.

EXAMPLE 21

99mTc (chlorine)(dimethyl glyoxime)3 4-methylphenyl boron

Following the procedure of example 2, but substituting p-toluene boronic acid for boric acid, yielded 88% of the title complex.

EXAMPLE 22

99mTc (chlorine)(dimethyl glyoxime)3 3-(1-piperidinyl)propyl boron

Into a 5 ml siliconized serum vial were measured 0.5 mg of dimethyl glyoxime in 0.1 ml of ethanol 1.0 mg of 3-(1-piperidinyl)propane boronic acid monohydrochloride, 0.2 ml of saturated sodium chloride, 10 mg of citric acid, and 50$\mu$l of saturated aqueous stannous pyrophosphate.

Sodium pertechnetate in physiological saline (0.2 ml) was added to the vial which was heated at 100° C. for 5 minutes yielding 75% of the title complex.

EXAMPLE 23

99mTc (bromine)(dimethyl glyoxime)3 3-(1-piperidinyl)propyl boron

Into a 5 ml siliconized serum vial were measured 1.0 mg of dimethyl glyoxime in 0.1 ml of ethanol, 5.0 mg of 3-(1-piperidinyl) propane boronic acid monohydrochloride, 0.4 ml of saturated potassium bromide, 10 mg of citric acid, and 50$\mu$l of saturated aqueous stannous pyrophosphate.

Sodium pertechnetate in physiological saline (0.2 ml) was added to the vial which was heated at 100° C. for 5 minutes yielding 13.8% of the title complex.

EXAMPLE 24

99mTc (chlorine)(dimethyl glyoxime)3 3-(4-methyl-1-piperidinyl)propyl boron

Following the procedure of example 23, but substituting 0.2 ml of saturated sodium chloride for potassium bromide and 5.0 mg of 3-(4-methyl-1-piperidinyl) propane boronic acid monohydrochloride for 3-(1-piperidinyl)propane boronic acid monohydrochloride, yielded 94% of the title complex.

EXAMPLE 25

99mTc (chlorine)(dimethyl glyoxime)3 3-(4-morpholinyl) propyl boron

Following the procedure of example 23, but substituting 0.2 ml of saturated sodium chloride for potassium bromide and 5.0 mg of 3-(4-morpholinyl)propane boronic acid monohydrochloride for 3-(1-piperidinyl) propane boronic acid monohydrochloride, yielded 87% of the title complex.

EXAMPLE 26

99mTc (chlorine)(dimethyl glyoxime)3 3-(4-benzylpiperidinyl)propyl boron

Following the procedure of example 23, but substituting 0.2 ml of saturated sodium chloride for potassium bromide and 5.0 mg of 3-(4-benzyl-1-piperidinyl) propane boronic acid monohydrochloride for 3-(1-piperidinyl) propane boronic acid monohydrochloride, yielded the title complex.

EXAMPLE 27

99mTc (chlorine)(dimethyl glyoxime)3 3-(5-dimethylamino-1-naphthalenesulfonylamino)phenyl boron Following the procedure of example 23, but substituting 0.2 ml of saturated sodium chloride for potassium bromide and 5.0 mg of 3-(5-dimethylamino-1-naphthalenesulfonylamino) benzene boronic acid monohydrochloride for 3-(1-piperidinyl) propane boronic acid monohydrochloride, yielded the title complex.

EXAMPLE 28

99mTc (chlorine) (dimethyl glyoxime)$_3$ 3-[methyl(2-phenylethyl)amino] propyl boron Following the procedure of example 23, but substituting 0.2 ml of saturated sodium chloride for potassium bromide and 5.0 mg of 3-(methyl(2-phenylethyl)amino) propane boronic acid for 3-(1-piperidinyl) propane boronic acid for 3-(1-piperidinyl) propane boronic acid monohydorchloide, yielded the title complex.

EXAMPLE 29

99mTc (chlorine)(dimethyl glyoxime)$_3$ 4-hydroxy-1-butenyl boron

Following the procedure of example 2, but substituting 4-hydroxy-1-butene boronic acid for boric acid, yielded the title compound.

EXAMPLE 30

99mTc (chlorine)(dimethyl glyoxime)$_3$ (4-benzyl1-piperidinyl) boron

Following the procedure of example 22, but substituting 5 mg of (4-benzyl-1-piperidinyl) boronic acid monohydrochloride for 3-(1-piperidinyl) propane boronic acid monohydrochloride yielded 83% of the title complex.

EXAMPLE 31

99mTc (chlorine)(dimethyl glyoxime)$_3$ 4-(bromomethyl)phenyl boron and 99mTc (chlorine) (dimethyl glyoxime)$_3$ 4-(ethoxymethyl)phenyl boron Following the procedure of example 22, but substituting 1 mg of 4-(bromomethyl)benzene boronic acid for 3-(1-piperidinyl)propane boronic acid, monohydrochloride, yielded less than 5% of 99mTc (chlorine)(dimethyl glyoxime)$_3$ 4-(bromomethyl)phenyl boron. The reaction also yielded 99mTc (chlorine) (dimethyl glyoxime)$_3$ 4-(ethoxymethyl)phenyl boron. The complexes were separated by HPLC.

EXAMPLE 32

99mTc (chlorine)(dimethyl glyoxime)$_3$ 2-phenylethyl boron

Following the procedure of example 2, but substituting 2-phenylethane boronic acid for boric acid, yielded the title complex.

EXAMPLE 33

99mTc (chlorine)(dimethyl glyoxime)$_3$ 4-(methoxymethyl)phenyl boron

Following the procedure of example 22, but substituting 1 mg of 4-(bromomethyl)benzene boronic acid for 3-(1-piperidinyl)propane boronic acid monohydrochloride and methanol for ethanol, yielded the title complex.

EXAMPLE 34

99mTc (chlorine)(dimethyl glyoxime)$_3$ 4-(butyloxymethyl)phenyl boron

Following the procedure of example 22, but substituting 1 mg of 4-(bromomethyl)benzene boronic acid for 3-(1-piperidinyl)propane boronic acid monohydrochloride and butanol for ethanol, yielded the title complex.

EXAMPLE 35

99mTc (chlorine)(1,2-cycloheptanedione dioxime)$_3$ methyl boron

Following the procedure of example 9, but substituting 1,2-cycloheptenedione dioxime for dimethyl glyoxime, yielded 92% of the title complex.

EXAMPLE 36

99mTc (chlorine)(dimethyl glyoxime)$_3$ 4-[(diethylamino)methyl]phenyl boron

Following the procedure of example 2, but substituting 4-[(diethylamino)methyl]benzene boronic acid monohydrochloride for boric acid, and adding 2.0 mg of diethylenetriamine pentacetic acid yielded 77% of the title complex.

EXAMPLE 37

99mTc (chlorine)(dimethyl glyoxime)$_3$ 4-(aminomethyl)phenyl boron

Following the procedure of example 2, but substituting 4-(aminomethyl)boronic acid monohydrochloride for 4-[(diethylamino)methyl]benzene boronic acid monohydrochloride, yielded 81% of the title complex.

EXAMPLE 38

99mTc (chlorine)(dimethyl glyoxime)$_3$ hexadecyl boron

Following the procedure of example 36, but substituting hexadecane boronic acid for 4-[(diethylamino)methyl]benzene boronic acid monohydrochloride, yielded the title complex.

EXAMPLE 39

99mTc (chlorine)(dimethyl glyoxime)$_3$ 17-octadecenoic acid, 18-boron

Following the procedure of example 2, but substituting 18-borono-17-octadecenoic acid for boric acid, yielded 62% of the title complex.

EXAMPLE 40

99mTc (chlorine)(dimethyl glyoxime)$_3$ 4-formylphenyl boron

Following the procedure of example 2, but substituting p-(benzaldehyde)boronic acid for boric acid, yields 47% of the title complex.

EXAMPLE 41

99mTc (chlorine)(dimethyl glyoxime)$_3$ 4-[[methyl (2-phenylethyl)amino]methyl]phenyl boron Following the procedure of example 2, but substituting 4-[[methyl(2-phenylethyl)amino]-methyl]benzene boronic acid monohydrochloride for boric acid, yielded the title complex.

EXAMPLE 42

99mTc (chlorine)(dimethyl glyoxime)$_3$ 4-ethylphenyl boron

Following the procedure of example 2, but substituting 4-ethylbenzene boronic acid for boric acid, yielded the title complex.

EXAMPLE 43

99mTc (chlorine)(dimethyl glyoxime)3
2,4-dimethylphenyl boron

Following the procedure of example 2, but substituting 2,4-dimethylbenzene boronic acid for boric acid, yielded the title complex.

EXAMPLE 44

99mTc (chlorine)(dimethyl glyoxime)3
4-[(dimethylamino)methyl]phenyl boron

Following the procedure of example 2, but substituting 4-[(dimethylamino)methyl]benzene boronic acid monohydrochloride for boric acid, yielded the title complex.

EXAMPLE 45 99mTc (chlorine)(dimethyl glyoxime)3 4-[(diisopropylamino)methyl]phenyl boron Following the procedure of example 2, but substituting 4-[(diisopropylamino)methyl]benzene boronic acid monohydrochloride for boric acid, yielded the title complex.

EXAMPLE 46

99mTc (chlorine)(1,2-cyclohexanedionedioxime)3
3-(1-piperidinyl)propyl boron

Into a 5 ml siliconized vial were measured 0.5 mg of 1,2-cyclohexanedione dioxime in 0.1 ml of ethanol, 1.0 mg of 3-(1-piperidinyl)propane boronic acid monohydrochloride, 0.2 ml of saturated sodium chloride, 10 mg of citric acid and 50$\mu$l of saturated stannous pyrophosphate.

Sodium pertechnetate in physiological saline (0.2 ml) was added to the vial which was then heated at 100° C. for 5 minutes yielding 84% of the title complex.

EXAMPLE 47 99mTc (chlorine)(1,2-cyclohexanedione dioxime)3 3-(4-methyl-1-piperidinyl)propyl boron Following the procedure of example 46, but substituting 3-(4-methyl-1-piperidinyl)propane boronic acid monohydrochloride for 3-(1-piperidinyl)propane boronic acid monohydrochloride, yielded 82% of the title complex.

EXAMPLE 48

99mTc (chlorine)(1,2-cyclohexanedione dioxime)3 3-(4-morpholinyl)propyl boron

Following the procedure of example 46, but substituting 3-(4-morpholinyl)propane boronic acid monohydrochloride for 3-(1-piperidinyl)propane boronic acid monohydrochloride, yielded 90% of the title complex.

EXAMPLE 49

99mTc (chlorine)(1,2-cyclohexanedione dioxime)3 3-aminophenyl boron

Following the procedure of example 46, but substituting 3-aminobenzene boronic acid monohydrochloride for 3-(1-piperidinyl)propane boronic acid monohydrochloride yielded 93% of the title complex.

EXAMPLE 50

99mTc (chlorine)(1,2-cyclohexanedione dioxime)3 3-(4-phenyl-1-piperidinyl) propyl boron Following the procedure of example 46, but substituting 5.0 mg of 3-(4-phenyl-1-piperidinyl)-propane boronic acid monohydrochloride for 3-(1-piperidinyl) boronic acid monohydrochloride and labeling with sodium pertechnetate in physiological saline (0.3 ml), yielded 84% of the title complex.

EXAMPLE 51

99mTc (bromime)(1,2-cyclohexanedione dioxime)3 3-(4-phenyl-1-piperidinyl) propyl boron Following the procedure of example 46, but substituting 5.0 mg of 3-(4-phenyl-1-piperidinyl)-propane boronic acid monohydrochloride for 3-(1-piperidinyl) propane boronic acid monohydrochloride and 100 mg of potassium bromide for sodium chloride yielded the title complex.

EXAMPLE 52

99mTc (chlorine)(1,2-cyclohexanedione dioxime)3 1-butyl boron

Following the procedure of example 46, but substituting 1-butane boronic acid for 3-(piperidinyl)propane boronic acid monohydrochloride and labeling with sodium pertechnetate in physiological saline (0.3 ml) yielded 69% of the title complex.

EXAMPLE 53

99mTc (chlorine)(1,2-cyclohexanedione dioxime)3 3-(5-dimethylamino-1-naphthalenesulfonylamino)phenyl boron Following the procedure of example 46, but substituting 3-(5-dimethylamino-1-naphthalenesulfonylamino)-benzene boronic acid for 3-(1-piperidinyl)propane boronic acid monohydrochloride and labeling with sodium pertechnetate in physiological saline (0.3 ml), yielded 80% of the title complex.

EXAMPLE 54

99mTc (chlorine)(1,2-ethanedione dioxime)3 3-(5-dimethylamino-1-naphthalenesulfonylamino)phenyl boron Following the procedure of example 53, but substituting 1,2-ethanedione dioxime for 1,2-cyclohexanedione dioxime, yielded 71% of the title compound.

EXAMPLE 55

99mTc (chlorine)(1,2-cyclohexanedione dioxime)3 methyl boron

Into a 5 ml siliconized serum vial were measured 2.0 mg of 1,2-cyclohexanedione dioxime in 0.2 ml of ethanol, 2.0 mg of methane boronic acid, 10 mg of citric acid, 100 mg of sodium chloride, 1.0 mg of diethylenetriamine pentaacetic acid, and 50–60 $\mu$g of anhydrous stannous chloride in 1$\mu$l of concentrated hydrochloric acid.

Sodium pertechnetate in physiological saline (0.5 ml) was added to the vial which was then heated at 100° C. for 5 minutes yielding 85% of the title complex.

EXAMPLE 56

99mTc (bromine)(1,2-cyclohexanedione dioxime)3 methyl boron

Following the procedure of example 55, but substituting potassium bromide for sodium chloride and labeling with sodium pertechnetate in physiological saline (0.1 ml), yielded the title complex.

EXAMPLE 57

99mTc (chlorine)(1,2-cyclohexanedione dioxime)3 4-ethylphenyl boron

Following the procedure of example 55, but substituting 4-ethylbenzene boronic acid for methane boronic acid, yielded the title complex.

EXAMPLE 58

99mTc (chlorine)(dimethyl glyoxime)3 4-[1-(diisopropylamino) ethyl]phenyl boron

Following the procedure of example 2, but substituting 4-[1-(diisopropylamino)ethyl] benzene boronic acid for boric acid, yielded the title complex.

EXAMPLE 59

99mTc (chlorine)(dimethyl glyoxime)3 4-[(isopropylamino) methyl]phenyl boron

Following the procedure of example 2, but substituting 4-[(isopropylamino)methyl]benzene boronic acid monohydrochloride for boric acid, yielded 8% of the title complex.

EXAMPLE 60

99mTc (chlorine)(1,2-cyclohexanedione dioxime)3 4-methylphenyl boron

Following the procedure of example 2, but substituting 4-toluene boronic acid for boric acid and 1,2-cyclohexanedione dioxime for dimethyl glyoxime, yielded the title complex.

EXAMPLE 61

99mTc (chlorine)(dimethyl glyoxime)3 2,4,6-trimethylphenyl boron

Following the procedure of example 2, but substituting 2,4,6-trimethylbenzene boronic acid for boric acid, yielded the title complex.

EXAMPLE 62

99mTc (chlorine)(dimethyl glyoxime)3 2-methyl-1-propyl boron

Following the procedure of example 2, but substituting 2-methyl-1-propane boronic acid for boric acid, yielded 84% of the title complex.

EXAMPLE 63

99mTc (chlorine)(1,2-cyclohexanedione dioxime)3 1-heptyl boron

Following the procedure of example 2, but substituting 1-heptane boronic acid for boric acid and 1,2-cyclohexanedione dioxime for dimethyl glyoxime, yielded the title complex.

EXAMPLE 64 99mTc (chlorine)(dimethyl glyoxime)3 9-carboxynonyl boron

Following the procedure of example 2, but substituting 10-borono decanoic acid for boric acid, yielded the title complex.

EXAMPLE 65

99mTc (chlorine)(1,2-cyclohexanedione dioxime)3 2-methyl-1-propyl boron

Following the procedure of example 2, but substituting 2-methyl-1-propane boronic acid for boric acid and 1,2-cyclohexanedione dioxime for dimethyl glyoxime, yield 85% of the title complex.

EXAMPLE 66

99mTc (chlorine)(1,2-cyclohexanedione dioxime)3 ethyl boron

Following the procedure of example 2, but substituting ethane boronic acid for boric acid and 1,2-cyclohexanedione dioxime for dimethyl glyoxime, yielded 88% of the title complex.

EXAMPLE 67

99mTc (chlorine)(dimethyl glyoxime)3 ethyl boron

Following the procedure of example 2, but substituting ethane boronic acid for boric acid, yielded 77% of the title complex.

EXAMPLE 68

99mTc (chlorine)(dimethyl glyoxime)3 3-methylphenyl boron

Following the procedure of example 2, but substituting 3-toluene boronic acid for boric acid yielded the title complex.

EXAMPLE 69

99mTc (chlorine)(dimethyl glyoxime)3 2-methylphenyl boron

Following the procedure of example 2, but substituting o-toluene boronic acid for boric acid yielded the title complex.

EXAMPLE 70

99mTc (chlorine)(dimethyl glyoxime)3 cyclopentyl boron

Following the procedure of example 2, but substituting cyclopentane boronic acid for boric acid, yielded the title complex.

EXAMPLE 71

99mTc (chlorine)(dimethyl glyoxime)3 2-butyl boron

Following the procedure of example 2, but substituting 2-butane boronic acid for boric acid, yielded the title complex.

EXAMPLE 72

99mTc (chlorine)(dimethyl glyoxime)3 4-methoxyphenyl boron

Following the procedure of example 2, but substituting 4-methoxybenzene boronic acid for boric acid, yielded the title complex.

EXAMPLE 73

99mTc (chlorine)(dimethyl glyoxime)3 4-(t-butyl)phenyl boron

Following the procedure of example 2, but substituting 4-(t-butane)benzene boronic acid for boric acid, yielded the title complex.

EXAMPLE 74

99mTc (chlorine)(1,2-ethanedione dioxime)3 1-butyl boron

Following the procedure of example 2, but substituting 1-butane boronic acid for boric acid 1,2-ethanedione dioxime for dimethyl glyoxime yielded 76% of the title complex.

EXAMPLE 75

99mTc (chlorine)(dimethyl glyoxime)₃ 4-(2-propyl)phenyl boron

Following the procedure of example 2, but substituting 4-(2-propane)benzene boronic acid for boric acid, yielded the title complex

EXAMPLE 76

99mTc (chlorine)(1,2-cyclohexanedione dioxime)₃ hydroxy boron

Following the procedure of example 2, but substituting 1,2-cyclohexanedione dioxime for dimethyl glyoxime, and omitting ethanol, yielded the title complex.

EXAMPLE 77

99mTc (chlorine)(α-furyldioxime)₃ methyl boron

Following the procedure of example 2, but substituting α-furyldioxime for dimethyl glyoxime, and methane boronic acid for boric acid, yielded the title complex.

EXAMPLE 78

99mTc (chlorine)(3-methyl-1,2-cyclopentanedione dioxime)₃ methyl boron

Following the procedure of example 2, but substituting 3-methyl-1,2-cyclopentanedione dioxime for dimethyl glyoxime and methane boronic acid for boric acid, yielded the title complex.

EXAMPLE 79

99mTc (chlorine)(1,2-cyclopentanedione dioxime)₃ methyl boron

Following the procedure of example 2, but substituting 1,2-cyclopentanedione dioxime for dimethyl glyoxime, and methane boronic acid for boric acid, yielded the title complex.

What is claimed is:

1. A boronic acid adduct of technetium-99m dioxime complexes having the formula $$99mTc\ X(Y)_3\ Z,$$

wherein
X is an anion;
Y is a vicinal dioxime having the formula

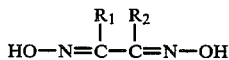

or a pharmaceutically acceptable salt thereof, wherein $R_1$ and $R_2$ are each independently hydrogen, halogen, alkyl, aryl, amino or a 5 or 6-membered nitrogen or oxygen containing heterocycle, or together $R_1$ and $R_2$ are $-(CR_8R_9)_n-$ wherein n is 3, 4, 5 or 6 and $R_8$ and $R_9$ are each independently hydrogen or alkyl; and
Z is a boron derivative of the formula $$B-R_3$$

wherein $R_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or $(R_4R_5N)$-alkyl and $R_4$ and $R_5$ are each independently hydrogen, alkyl, or arylalkyl, or $R_4$ and $R_5$ when taken together with the nitrogen atom to which they are attached form a 5 or 6-membered nitrogen containing heterocycle.

2. A boronic acid adduct in accordance with claim 1, wherein X is a halide.
3. A boronic acid adduct in accordance with claim 1, wherein X is chloride or bromide.
4. A boronic acid adduct in accordance with claim 1, wherein X is chloride.
5. A boronic acid adduct in accordance with claim 1, wherein Y is dimethyl glyoxime, 1,2-cyclohexanedione dioxime, 1,2-ethanedione dioxime, α-furyldioxime, 1,2-cyclopentanedione dioxime, or 3-methyl-1,2-cyclopentanedione dioxime.
6. A boronic acid adduct in accordance with claim 1, wherein Y is dimethyl glyoxime
7. A boronic acid adduct in accordance with claim 1, wherein Y is 1,2-cyclohexanedione dioxime.
8. A boronic acid adduct in accordance with claim 1, wherein Y is 1,2-ethanedione dioxime.
9. A boronic acid adduct in accordance with claim 1, wherein Y is α-furyldioxime.
10. A boronic acid adduct in accordance with claim 1, wherein the boron derivative Z is B-alkyl.
11. A boronic acid adduct in accordance with claim 1, wherein the boron derivative Z is B-alkoxy.
12. A boronic acid adduct in accordance with claim 1, wherein the boron derivative Z is B-benzyl.
13. A boronic acid adduct in accordance with claim 1, wherein the boron derivative Z is B-cycloalkyl.
14. The boronic acid adduct in accordance with claim 1, 99mTc (chlorine) (1,2-cyclohexanedione dioxime)₃ methyl boron.
15. The boronic acid adduct in accordance with claim 1, 99mTc (chlorine)(dimethyl glyoxime)₃ 1-methylpropyl boron.
16. The boronic acid adduct in accordance with claim 1, 99mTc (chlorine)(dimethyl glyoxime)₃ 4-methylphenyl boron.
17. The boronic acid adduct in accordance with claim 1, 99mTc (chlorine)(dimethyl glyoxime)₃ cyclopentyl boron.
18. The boronic acid adduct in accordance with claim 1, 99mTc (chlorine) 1,2-cyclohexanedione dioxime)₃ ethyl boron.
19. The boronic acid adduct in accordance with claim 1, 99mTc (chlorine)(dimethyl glyoxime)₃ 4-(t-butyl)-phenyl boron.
20. The boronic acid adduct in accordance with claim 1, 99mTc (chlorine) (dimethyl glyoxime)₃ 2-methyl-1-propyl boron.
21. The boronic acid adduct in accordance with claim 1, 99mTc (chlorine) (1,2-cyclohexanedione dioxime)₃ hydroxy boron.
22. A kit suitable for labeling with technetium-99m, said kit comprising:
(i) a source of anion;
(ii) a boronic acid derivative, or compounds which can react in situ to form a boronic acid derivative, having the formula

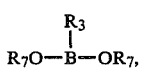

or a pharmaceutically acceptable salt thereof, wherein $R_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxy-alkenyl, haloalkyl, haloalkenyl, aryl, arylalkyl, or $R_4R_5N$-alkyl and $R_4$ and $R_5$ are each independently hydrogen, alkyl, or arylalkyl, or $R_4$ and $R_5$ when taken together with nitrogen atom to which they are attached form a 5 or 6-membered nitrogen containing heterocycle, and $R_7$ is hydrogen, alkyl or aryl;

(iii) a dioxime having the formula

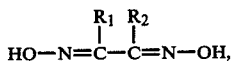

or a pharmaceutically acceptable salt thereof, wherein $R_1$ and $R_2$ are each independently hydrogen, halogen, alkyl, aryl, amino or a 5 or 6-membered nitrogen or oxygen containing heterocycle, or together $R_1$ and $R_2$ are $-(CR_8R_9)_n-$ wherein n is 3, 4, 5 or 6 and $R_8$ and $R_9$ are each independently hydrogen or alkyl; and (iv) a reducing agent.

23. A kit in accordance with claim 22, wherein the source of anion is a source of halide.

24. A kit in accordance with claim 22, wherein the source of anion is a source of chloride or bromide.

25. A kit in accordance with claim 22 wherein the dioxime is dimethyl glyoxime, 1,2-cyclohexanedione dioxime, 1,2-ethanedione dioxime or α-furyldioxime.

26. A kit in accordance with claim 22, wherein the dioxime is dimethyl glyoxime.

27. A kit in accordance with claim 22, wherein the dioxime is 1,2-cyclohexanedione dioxime.

28. A kit in accordance with claim 22, wherein the reducing agent is a stannous salt.

* * * * *